United States Patent [19]

Kappes et al.

[11] Patent Number: 5,508,394

[45] Date of Patent: Apr. 16, 1996

[54] CITRIC ESTERS OF POLYHYDROXY COMPOUNDS AND USE THEREOF IN DETERGENTS

[75] Inventors: Elisabeth Kappes, Mannheim; Alfred Oftring, Bad Durkheim; Richard Baur, Mutterstadt; Alexander Kud, Eppelsheim; Dieter Boeckh; Heinrich Hartmann, both of Limburgerhof; Volker Schwendemann, Neustadt, all of Germany

[73] Assignee: BASF Aktiengesellschaft, Ludwigshafen, Germany

[21] Appl. No.: 117,134

[22] PCT Filed: Mar. 7, 1992

[86] PCT No.: PCT/EP92/00512

§ 371 Date: Sep. 16, 1993

§ 102(e) Date: Sep. 16, 1993

[87] PCT Pub. No.: WO92/16493

PCT Pub. Date: Oct. 1, 1992

[30] Foreign Application Priority Data

Mar. 16, 1991 [DE] Germany ............... 41 08 626.0

[51] Int. Cl.$^6$ ............... C07H 5/04; C07H 5/06; C07H 13/02; A01N 43/04

[52] U.S. Cl. ............... 536/55.2; 536/115; 536/116; 536/119; 536/120; 536/123.1; 536/123.13; 568/864; 568/865; 560/182

[58] Field of Search ............... 536/115, 55.2, 536/116, 119, 120, 123.1, 123.13; 568/864, 865; 560/182

[56] References Cited

U.S. PATENT DOCUMENTS

| | | | |
|---|---|---|---|
| 2,813,892 | 11/1957 | Mehltretter | 560/182 |
| 3,563,903 | 2/1971 | Schmadel et al. | 252/546 |
| 3,661,955 | 5/1972 | Centolella et al. | 560/182 |
| 3,859,224 | 1/1975 | Kandler et al. | 252/135 |
| 3,872,020 | 3/1975 | Yamagishi et al. | 536/119 |
| 4,797,481 | 1/1989 | Garlisi et al. | 536/123.1 |

FOREIGN PATENT DOCUMENTS

| | | |
|---|---|---|
| 0258814 | 3/1988 | European Pat. Off. . |
| 0433010 | 6/1991 | European Pat. Off. . |
| 894752 | 4/1962 | United Kingdom . |

OTHER PUBLICATIONS

Derwent Abstracts, AN 77–38805Y, JP 52049203, Apr. 20, 1977.

*Primary Examiner*—Douglas W. Robinson
*Assistant Examiner*—Everett White
*Attorney, Agent, or Firm*—Oblon, Spivak, McClelland, Maier & Neustadt

[57] ABSTRACT

Esters of citric acid or acetylcitric anhydride with compounds of at least 3 OH groups selected from the group consisting of polyglycerol, sugarcarboxylic acids, alkyl glucosides, derivatives of oligosaccharides, aminosorbitol, aminodisorbitol, glucosamine, triethanolamine and trishydroxyethylmelamine, each OH group of the alcohol component of the esters being esterified on average with from 0.15 to 1 molecule of citric acid or acetylcitric anhydride, are useful as additives in low-phosphate or phosphate-free detergents.

10 Claims, No Drawings

CITRIC ESTERS OF POLYHYDROXY COMPOUNDS AND USE THEREOF IN DETERGENTS

It is an object of the present invention to provide novel substances. It is a further object of the present invention to provide detergent additives which are improved compared with the prior art.

We have found that the first object is achieved by esters of citric acid or acetylcitric anhydride and polyhydroxy compounds, which are obtainable by esterifying (a) citric acid or acetylcitric anhydride with (b) a compound of at least 3 OH groups selected from the group consisting of sugarcarboxylic acids, $C_2$–$C_5$-alkylglucosides, hydroxy-alkylglucosides, sugar alcohols and oxidation products of oligosaccharides which contain up to 4 monosaccharide units, amino-sorbitol, sorbitol, aminodisorbitol, glucosamine, N-acetylglucosamine and trishydroxyethylmelamine, each OH group of compound (b) being on average esterified with from 0.15 to 1 molecule of a compound (a). We have found that the second object is achieved by using citric esters as additives in low-phosphate or phosphate-free detergent formulations in an amount of from 0.1 to 30% by weight, based on the formulation.

The citric esters are prepared by reacting the components described above under (a) and (b). This reaction is customarily carried out using the known acidic catalysts for esterifications, eg. sulfuric acid, paratoluenesulfonic acid, benzenesulfonic acid or hydrochloric acid. However, in principle, it can also be carried out without a catalyst. The citric acid can also be partially neutralized prior to the esterification, preferably in the course of reaction with natural substances or derivatives thereof; for example, 1 mol of citric acid is neutralized with from 0.1 to 2.9, preferably from 0.5 to 2.0, mol of a monoacid base, e.g. NaOH. The esterification can be carried out in substance, i.e. by heating the components (a) and (b) and distilling off water, or else in the presence of an inert diluent. The inert diluent, e.g. toluene, xylene or isopropylbenzene, here acts by means of the amount of water which has distilled off, the acid number and the saponification number of samples of the reaction mixture. The esterification in substance is preferably carried out in a kneading reactor. In general, the esterification is carried out in a kneader when relatively viscous esterification products are formed. Depending on the ratio of the components (a) and (b) and depending on the degree of conversion of the esterification, it is also possible to prepare linear or branched oligomeric esters from a plurality of building blocks conforming to (a) and (b).

As sugarcarboxylic acids, it is possible to use the oxidation products of sugars of from 4 to 7 carbon atoms, e.g. gluconic acid, glucoheptonic acid, glucaric acid, galactaric acid, glucuronic acid or mannonic acid and also the corresponding lactones, e.g. gluconolactone and glucoheptonolactone.

Suitable compounds (b) also include alkylglucosides and alkylpolyglucosides, alkylmaltosides and alkylmaltotriosides. The alkyl group can be a $C_2$–$C_5$, preferably a $C_2$–$C_4$-alkyl group, e.g. ethyl, n-propyl, isopropyl, n-butyl or isobutyl. The alkyl group can also be substituted, for example by hydroxyl. Suitable compounds of this type are for example hydroxyethyl glucoside and hydroxypropyl glucoside and also the corresponding polyglucosides. The polyglucosides contain an average of from 1.1 to 10, preferably from 1.3 to 3, glucoside units.

Oligosaccharides which contain up to 4 monosaccharide units are for example maltose, maltotriose, maltotetraose, saccharose, lactose, leucrose, isomaltulose, chitobiose, chitotriose, chitotetraose and the derivatives obtainable therefrom by loss of the acetyl groups. The monosaccharide units of the oligosaccharides can come from any customary monosaccharide, in particular from glucose, galactose, fructose or mannose. Sugar alcohols of oligosaccharides which contain up to 4 monosaccharide units are obtainable from the above-mentioned oligosaccharides by reduction. The oxidation products of the oligosaccharides mentioned include for example saccharosetricarboxylic acid and lactobionic acid.

Further suitable compounds of group (b) are aminosorbitol, aminodisorbitol, glucosamine, N-acetylglucosamine, triethanolamine and trishydroxyethylmelamine. Preferred OH-containing compounds of component (b) are gluconic acid, aminosorbitol, glucoheptonic acid, maltose and hydroxyethyl glucoside.

Immediately following esterification, the citric esters are present in the acid form. They can be converted into the salt form by addition of bases. Suitable bases are for example sodium hydroxide, potassium hydroxide, lithium hydroxide, calcium hydroxide, sodium carbonate, potassium carbonate, lithium carbonate, calcium carbonate, ammonium carbonate, ammonium bicarbonate, ammonia, ethanolamine, diethanolamine or triethanolamine. The bases are preferably used in the form of aqueous solutions. Of the bases mentioned, sodium hydroxide, sodium carbonate and sodium bicarbonate are preferred. The citric esters are neutralized to such an extent that the aqueous solutions of the neutralized or partially neutralized citric esters have pH values within the range from 3.0 to 8.5, preferably from 4.5 to 7. The citric esters to be used according to the present invention have acid numbers of about 90–780, preferably 265–740 mg of KOH/g of citric ester. The citric esters to be used according to the invention have an acid number: saponification number ratio within the range from 0.33 to 0.85, preferably from 0.5 to 0.8, if the polyhydroxy compound b) used contains no acid groups. If it does contain acid groups, the acid number thus introduced in the preparation of the polyester must be taken into account when determining the ratio of acid number to saponification number in that the stated limits will shift accordingly. The sodium salts of the esters can be isolated in the form of amorphous solids for example from an alcoholic solution, spray drying or fluidized bed drying. The drying can be effected with or without the addition of detergent-active substances. For instance, by fluidized bed drying of mixtures with anionic surfactants, polymeric detergent additives, builders or diluents it is possible to prepare a granular product which contains the citric esters to be used according to the present invention. This form of formulation can be of decisive advantage for use of the citric esters in alkaline or acid detergents.

The above-described citric esters are used as additives in pulverulent and liquid detergents, preferably in phosphate-free or low-phosphate detergents which contain not more than 25% by weight of sodium triphosphate. The citric esters are used in amounts of from 0.1 to 30, preferably from 0.5 to 15,% by weight, based on the detergent formulation. The citric esters to be used according to the present invention are good dispersants for clay in the washing liquor. This property is important because loamy soiling of textile material is very common. The citric esters act as builders in detergent formulations, augment the detergency of the surfactants in detergents and also bring about during the wash a reduction in the incrustation of the washed textile material and make a significant contribution to the dispersal of soil in the washing liquor. The citric esters are biodegradable to a high extent, for example to more than 90%.

The compositions of detergent formulations used for washing can differ greatly. The same is true of those used as cleaners. Both washing and cleaning detergent formulations customarily contain surfactants with or without builders. This is true not only of liquid but also of pulverulent washing and cleaning detergent formulations. Examples of the compositions of washing detergent formulations customary in Europe, the USA and Japan may be found for example in table form in Chemical and Engineering News 67 (1989), 35.

The above-described citric esters are used according to the invention in detergents which contain up to 45% by weight of phosphate, although their use in detergents having a reduced phosphate content (which is to be understood as meaning a phosphate content of less than 25% by weight of sodium triphosphate) or in phosphate-free detergents is preferred. The citric esters can be added to the detergent formulation in the form of granules, in the form of pastes, as a highly viscous mass, as a dispersion or as a solution in a solvent. The citric esters can also be adsorbed on the surface of diluents, for example sodium sulfate, or builders (zeolites or bentonites) and also on other solid constituents of the detergent formulation.

The detergent formulations in question are pulverulent or liquid. They can differ in composition by region and according to the specific intended use.

Universal household detergents for drum type washing machines of the type widely used in Europe usually contain from 5 to 10% by weight of anionic surfactants, from 1 to 5% by weight of nonionic surfactants, from 1 to 5% by weight of foam regulators, such as silicone oils or soaps, from 0 to 40% by weight of a water softener, such as sodium carbonate or pentasodium triphosphate, which may be replaced in whole or in part by the compounds of the present invention, from 0 to 30% by weight of an ion exchanger such as zeolite A, from 2 to 7% by weight of sodium silicates as corrosion-inhibitors, from 10 to 30% by weight of bleaching agents, such as sodium perborate or sodium percarbonate, organic per-acids and salts thereof, from 0 to 5% by weight of bleach activators, such as tetraacetylethylenediamine, pentaacetylglucose, hexaacetylsorbitol or acyloxy-benzenesulfonate, stabilizers, such as magnesium silicate or ethylenediaminetetraacetate, grayhess inhibitors, such as carboxymethylcellulose, methylalkylcelluloses and hydroxyalkylcelluloses, vinyl acetate-grafted polyglycols, oligomeric and polymeric terephthalic acid/ethylene glycol/polyethylene glycol esters, enzymes, fluorescent whitening agents, scents, fabric softeners, dyes, and diluents.

By contrast, the heavy duty detergents which are used in the USA, Japan and neighboring countries in tub type washing machines are usually free of bleaching agents, but on the other hand their anionics content is two to three times higher and they contain more wash alkalis, such as sodium carbonate and sodium silicates (in general up to 25% by weight) and mostly they also lack the bleach activators and bleach stabilizers. The levels of surfactants and other ingredients can be appreciably higher in the case of detergent concentrates, which are available with little or no diluent. Detergents for delicate and colored fabrics, wool detergents and hand washing detergents likewise usually contain no bleaching agents and only low levels of alkaline ingredients together with a correspondingly higher surfactant content.

Detergents for the commercial laundry sector are designed for the special conditions of industrial washing (soft water, continuous washing) which make it possible to customize the detergent to the type of article being washed and to the nature of the soil. Combinations are therefore used in which one ingredient predominates or others are completely absent only to be added separately when required. For this reason the surfactants, builders, alkalis and bleaching agents of these detergents vary within wide limits.

Suitable anionic surfactants for the afore-mentioned pulverulent washing detergents, or washing powders, are for example sodium alkylbenzenesulfonates, fatty alcohol sulfates and fatty alcohol polyglycol ether sulfates. Individual compounds of this type are for example $C_8$–$C_{12}$-alkylbenzenesulfonates, $C_{12}$–$C_{16}$-alkane-sulfonates, $C_{12}$–$C_{16}$-alkyl sulfates, $C_{12}$–$C_{16}$-alkyl sulfosuccinates and sulfated ethoxylated $C_{12}$–$C_{16}$-alkanols. Other suitable anionic surfactants are sulfated fatty acid alkanolamines, α-sulfo fatty acid esters, fatty acid monoglycerides or reaction products of from 1 to 4 mol of ethylene oxide with primary or secondary fatty alcohols or alkylphenols. Further suitable anionic surfactants are fatty acid esters and fatty acid amides of hydroxy- or amino-carboxylic or—sulfonic acids, for example the fatty acid sarcosides, glycolates, lactates, taurides or isethionates. The anionic surfactants can be present in the form of the sodium, potassium and ammonium salts and also as soluble salts of organic bases, such as mono-, di- or triethanolamine or other substituted amines. The group of anionic surfactants also includes the ordinary soaps, i.e. the alkali metal salts of natural fatty acids.

Suitable nonionic surfactants (nonionics) are for example addition products of from 3 to 40, preferably from 4 to 20, mol of ethylene oxide with 1 mol of fatty alcohol, alkylphenol, fatty acid, fatty amine, fatty acid amide or alkanesulfonamide. The abovementioned addition products of ethylene oxide may additionally contain up to 90% by weight, based on cocondensed ethylene oxide and propylene oxide, of propylene oxide as cocondensed units. The addition products which contain ethylene oxide and propylene oxide as cocondensed units may be modified by incorporation of butylene oxide as cocondensed units in amounts of up to 60% by weight, based on the total alkylene oxide content. Of particular importance are the addition products of from 5 to 16 mol of ethylene oxide with coconut or tallow fatty alcohols, with oleyl alcohol or with synthetic alcohols of from 8 to 18, preferably from 12 to 18, carbon atoms, and also with mono- or dialkylphenols having from 6 to 14 carbon atoms in the alkyl moieties. Besides these water-soluble nonionics, however, it is also possible to use water-insoluble or incompletely water-soluble polyglycol ethers having from 1 to 4 ethylene glycol ether moieties in the molecule, in particular if they are used together with water-soluble nonionic or anionic surfactants.

Further usable nonionic surfactants are the water-soluble addition products of ethylene oxide with polypropylene glycol ethers, alkylenediaminopolypropylene glycol and alkylpolypropylene glycols having 1 to 10 carbon atoms in the alkyl chain that contain from 20 to 250 ethylene glycol ether groups and from 10 to 100 propylene glycol ether groups, the polypropylene glycol ether chain acting as hydrophobe.

It is also possible to use nonionic surfactants of the type of the amine oxides or sulfoxides or the alkylpolyglucosides R-(Glu)$_x$, where R=$C_8$–$C_{16}$[Glu=glucose unit] and x=1–10.

The foaming power of the surfactants can be increased or reduced by combining suitable surfactant types. A reduction can also be achieved by adding non-surfactant-like organic substances.

Further possible formulation ingredients of detergents include monomeric, oligomeric and polymeric phosphonates, ether sulfonates based on unsaturated fatty alcohols, e.g. oleyl alcohol ethoxylate butyl ether and alkali metal salts thereof. These substances can be characterized for example with the aid of the formula RO(CH$_2$CH$_2$O)$_n$C$_4$H$_8$SO$_3$Na, where n is from 5 to 40 and R is oleyl.

The above-described citric esters can also be used as additives in liquid washing detergents. Citric esters preferably used in liquid washing detergents contain as component (b) polyglycerols containing from 3 to 10 glycerol units, gluconic acid, glucoheptonic acid, maltose and hydroxyethylglucoside as cocondensed units. Liquid detergents contain liquid surfactants or else solid surfactants which are soluble or at least dispersible in the detergent formulation. Suitable surfactants for this purpose are those products which are also used in pulverulent detergents but also liquid polyalkylene oxides or polyalkoxylated compounds. If the polyacetals are not directly miscible with the other constituents of the liquid detergent, it is possible to prepare homogeneous mixtures with the aid of a small amount of a solubilizer, for example water or a water-miscible organic solvent, e.g. isopropanol, methanol, ethanol, glycol, diethylene glycol or triethylene glycol or corresponding propylene glycols. The amount of surfactant in liquid detergents is within the range from 4 to 50% by weight, based on the formulation as a whole, since in liquid detergents, too, the proportions of the ingredients vary within wide limits according to regional market conditions or the intended application.

Liquid detergents may contain water in amounts of from 10 to 60, preferably from 20 to 50, % by weight. However, they can also be free of water.

Water-free liquid detergents may also contain suspended or dispersed peroxo compounds for bleaching. Examples of suitable peroxo compounds are sodium perborate, peroxocarboxylic acids and polymers having some peroxo-containing groups. Liquid detergents may also contain hydrotropes. These are compounds such as 1,2-propanediol, cumenesulfonate and toluenesulfonate. If such compounds are used for modifying a liquid detergent, their amount is from 2 to 5% by weight, based on the total weight of the liquid detergent. In many cases an addition of complexing agents has also proved advantageous for modifying pulverulent and liquid detergents. Complexing agents are for example ethylenediaminetetraacetic acid, nitrilotriacetate and isoserinediacetic acid and also phosphonates, such as aminotrismethylenephosphonic acid, hydroxyethanediphosphonic acid, ethylenediaminetetra-ethylenephosphonic acid and salts thereof. Complexing agents are used in amounts of from 0 to 10% by weight, based on the detergent. The detergents may also contain citrates, di—or triethanolamine, or opacifiers, fluorescent whitening agents, enzymes, perfume oils and dyes. These substances, if they are used for modifying a liquid detergent, together account for up to 5% by weight. The detergents are preferably phosphate-free. However, they may also contain phosphates, for example pentasodium triphosphate and/or tetrapotassium pyrophosphate. If phosphates are used, they account for up to 45, preferably up to 25, % by weight of the total formulation of the detergent.

The citric esters to be used according to the present invention can also interact with other known detergent additives (for example grayness inhibitors, clay dispersants and a substances which augment the primary detergency, color transfer inhibitors, bleach activators) in pulverulent and liquid detergents (phosphate-containing and phosphate-free) to produce synergistic effect enhancing not only the dispersal of particular soil but also the effectiveness of the other detergent additive.

The percentage in the examples are by weight.

EXAMPLE 1

97.2 g of a 50.4% strength aqueous solution of gluconic acid and 262.5 g of citric acid monohydrate are are heated to the boil in a 2-liter three-necked flask with 225 ml of xylene and with stirring. 93.6 g of water are distilled off azeotropically by means of a water separator. Then the xylene is decanted off, and the xylene still adhering to the reaction product is removed by distillation under reduced pressure. The remaining viscous product is dissolved in 670 ml of methanol. A 35% strength methanolic solution of a citric ester having an acid number of 210 mg of KOH/g and a saponification number of 285 mg of KOH/g was obtained. The methanolic solution was decolorized by means of active charcoal and then neutralized with sodium carbonate solution. The sodium salt of a gluconic-citric ester having an acid number of 10 mg of KOH/g and a saponification number of 209 mg of KOH/g was obtained.

EXAMPLE 2

128.3 g of a 50.4% strength aqueous solution of gluconic acid and 210 g of citric acid monohydrate are heated to 120°–140° C. with stirring. 98.4 g of water was distilled off. To speed up the distillation it can be carried out under reduced pressure, for example at 400 mbar. The ester obtained has an acid number of 535 mg of KOH/g and a saponification number of 756 mg of KOH/g. The reaction product is then dissolved in water and adjusted to pH 6.5 with 20% strength sodium carbonate solution. The aqueous solution is freeze dried to obtain the sodium salt of the ester having an acid number of 13 mg of KOH/g and a saponification number of 188 mg of KOH/g.

EXAMPLE 3

90 g of maltose are reacted with 525 g of citric acid monohydrate and toluene as entrainer as described in Example 1. After about half of the water formed in the course of the reaction has distilled off, 6 g of the monooleic ester of triethanolamine (water-in-oil emulsifier) are added to the reaction mixture. This makes the reaction mixture more stirrable. The reaction product has an acid number of 539 mg of KOH/g and a saponification number of 789 mg of KOH/g. It is dissolved in water, adjusted to pH 6.7 with sodium carbonate solution and unfreeze dried. The saponification number of the salt is 214 mg of KOH/g.

EXAMPLE 4

181 g of aminosorbitol and 1260 g of citric acid monohydrate are reacted as described in Example 1. 216 g of water are distilled off to obtain a product having an acid number of 512 mg of KOH/g and a saponification number of 745 mg of KOH/g. The sodium salt obtained therefrom has an acid number of <10 mg of KOH/g and a saponification number of 201 mg of KOH/g.

EXAMPLE 5

34.5 g of aminodisorbitol and 210 g of citric acid monohydrate are reacted as described in Example 1.

36 g of water are distilled off to obtain a product having an acid number of 525 mg of KOH/g and a saponification number of 782 mg of KOH/g. The sodium salt obtained therefrom has an acid number of <10 mg of KOH/g and a saponification number of 234 mg of KOH/g.

EXAMPLE 6

90 g of a hydroxyethylpolyglucoside having a degree of glucosidation of 1.3 and 420 g of citric acid monohydrate are reacted as described in Example 3. Hydroxyethylpolyglucoside was prepared as described in Tenside Detergents 10 (1973), 2.72 g of water are distilled off. The reaction product has an acid number of 518 mg of KOH/g and a saponification number of 760 mg of KOH/g. It is dissolved in water, adjusted to pH 6.7 with sodium carbonate solution and freeze dried. The saponification number of the salt is 204 mg of KOH/g.

CLAY DISPERSION

The removal of particulate soil from fabric surfaces is augmented by the presence of polyelectrolytes. Stabilizing the dispersion which forms as the particles are detached from the fabric surface is an important function of these polyelectrolytes. The stabilizing effect of the anionic dispersants is due to the fact that, as a consequence of the adsorption of dispersant molecules on the surfaces of the solids, the surface charge thereof and hence the repulsion increases. Further factors having a bearing on the stability of a dispersion include steric effects, the temperature, the pH and the electrolyte concentration.

The clay dispersion (CD) test described hereinafter can be used to assess the dispersing power of various polyelectrolytes in a simple manner. CD test Particulate soil is represented by finely ground china clay SPS 151.1 g of clay is intensively dispersed in 98 ml of water in a 100 ml cylinder in the presence of 1 ml of a 0.1% strength sodium salt solution of the polyelectrolyte for 10 minutes. Immediately after the stirring has been stopped, a sample of 2.5 ml is removed from the center of the cylinder and diluted to 25 ml and the turbidity measured in a turbidimeter. After the dispersion has stood for 30 and 60 minutes, further samples are taken and again measured in the turbidimeter. The turbidity of the dispersion is reported in nephelometric turbidity units (NTUs). The less the dispersion settles on storage, the higher the measured turbidity values are and the stabler the dispersion is. The second physical parameter determined is the dispersion constant $\tau$, which describes the time course of the sedimentation process. Since the sedimentation process approximates to a monoexponential time law, $\tau$ indicates the time within which the turbidity decreases to 1/e-th of the original level at time $\tau=0$.

The higher the value of $\tau$, the slower the rate of sedimentation in the dispersion.

The CD test was carried out for the sodium salts of the esters obtained as described in the Examples. The results are indicated below in the Table.

COMPARATIVE EXAMPLE 1

Glycerol tricitrate as described in Example 1 of DE-B-2 147 778.

COMPARATIVE EXAMPLE 2

Sorbitol hexacitrate as described in DE-B-2 147 778.

The compounds described in the Comparative Examples were likewise subjected to a CD test. The results obtained are indicated in the Table.

TABLE

| product | In-test substance: Sodium salt of reaction of Example | Turbidity after storage at once | 30 min | Dispersion constant $\tau$ 60 min |
|---|---|---|---|---|
| Example | | | | |
| 7 | 1 | 710  620 | 580 | 330 |
| 8 | 2 | 690  650 | 580 | 383.6 |
| 9 | 3 | 760  680 | 610 | 272.8 |
| 10 | 4 | 730  620 | 550 | 215 |
| 11 | 5 | 750  630 | 570 | 231.9 |
| 12 | 6 | 710  620 | 570 | 286.1 |
| Comparative Example | | | | |
| 1 | Glycerol tricitrate | 670  550 | 470 | 170 |
| 2 | Sorbitol hexacitrate | 700  600 | 490 | 172.6 |
| 3 | — | 600  37 | 33 | 41.4 |

As a comparison of the results of Examples 7 to 2 with the result of Comparative Examples 1 and 2 shows, the sodium salts of the citric esters described herein show distinctly improved clay dispersing power compared with the citrates known from DE-B-2 147 778.

We claim:
1. A detergent composition comprising a surfactant selected from the group consisting of anionic and nonionic surfactants, and from 0.1 to 30% by weight of at least one builder, said builder comprising a citric acid ester prepared by esterifying
   (a) citric acid or acetylcitric anhydride with
   (b) a compound of at least 3 OH groups selected from the group consisting of sugarcarboxylic acids, $C_2$–$C_4$-alkylglucosides, hydroxy-$C_2$–$C_4$-alkyl glucosides, carboxyl group containing oxidation products of oligosaccharides which contain up to 4 monosaccharide units,
   aminosorbitol, aminodisorbitol, glucosamine, N-acetylglucosamine and trishydroxyethylmelamine, wherein each OH group of compound (b) has an average esterification of 0.15 to 1 with a compound (a).

2. The detergent composition of claim 1 wherein said compound (b) is selected from the group consisting of aminosorbitol, aminodisorbitol, glucosamine, N-acetylglucosamine and trishydroxylethylmelamine.

3. The detergent composition of claim 1 wherein said compound (b) is a carboxyl group containing oxidation product of an oligosaccharide containing up to 4 monosaccharide units.

4. A detergent composition as set forth in claim 1 wherein said compound (b) is selected from the group consisting $C_2$–$C_4$-alkylglucosides and hydroxy-$C_2$–$C_4$-alkylglucosides.

5. A detergent composition of claim 1 wherein said compound (b) is a sugarcarboxylic acid and said citric acid ester is in the form of a sodium salt.

6. An ester of citric acid or acetylcitric anhydride and a polyhydroxy compound, which ester is the esterification reaction product of (a) citric acid or acetylcitric anhydride with (b) a compound of at least 3 OH groups selected from the group consisting of $C_2$–$C_4$-alkylglucosides, hydroxy-$C_2$–$C_4$-alkylglucosides, carboxyl group containing oxidation products of oligosaccharides which contain up to 4 monosaccharide units, aminosorbitol, aminodisorbitol, glucosamine, acetylglucosamine and trishydroxyethylmelamine, wherein each OH group of compound (b) has an average esterification of 0.15 to 1 with a compound (a).

7. The ester of claim 6 wherein said compound (b) is selected from the group consisting of $C_2$–$C_4$-alkylglucosides and hydroxy-$C_2$–$C_4$-alkylglucosides.

8. The ester of claim 6 wherein said compound (b) is a carboxyl group containing oxidation product of an oligosaccharide which contains up to 4 monosaccharide units.

9. The ester of claim 6 wherein said compound (b) is selected from the group consisting of aminosorbitol, aminodisorbitol, glucosamine, N-acetylglucosamine and trishydroxyethylmelamine.

10. A sodium salt of an ester of citric acid or acetylcitric anhydride and a polyhydroxy compound, which ester is the esterification reaction product of (a) citric acid or acetyl citric anhydride with (b) a sugarcarboxylic acid containing at least 3 OH groups, wherein each OH group of the sugarcarboxylic acid has an average esterification of 0.15 to 1 with a compound (a).

* * * * *